United States Patent

Koch

Patent Number: 5,873,819
Date of Patent: Feb. 23, 1999

[54] PNEUMATIC OTOSCOPE

[76] Inventor: Craig S. Koch, 6176 Reservoir Ct., Granite Bay, Calif. 95746

[21] Appl. No.: 72,041

[22] Filed: May 4, 1998

[51] Int. Cl.⁶ ..................................................... A61B 1/227
[52] U.S. Cl. ........................................... 600/200; 600/199
[58] Field of Search ...................................... 600/200, 199

[56] References Cited

U.S. PATENT DOCUMENTS

| | | | |
|---|---|---|---|
| 1,618,970 | 3/1927 | De Zeng | 600/200 |
| 1,636,463 | 7/1927 | De Zeng | 600/200 |
| 2,039,546 | 5/1936 | McGerry | 600/200 |
| 5,038,755 | 8/1991 | Burgio et al. | 600/200 |
| 5,345,926 | 9/1994 | Chikama | 600/200 |

*Primary Examiner*—Paul J. Hirsch
*Attorney, Agent, or Firm*—Donald E. Nist

[57] ABSTRACT

The pneumatic otoscope includes a speculum which has an elongated preferably generally cylindrical body with a rear end to which a vewing lens is fixed to seal that end. The opposite front end of the speculum is open. The sidewall of the speculum body is closed and defines a generally central space extending from the rear end to the front end of the body. The speculum body also has at least one opening extending peripherally through the sidewall. To the front end of the speculum body is secured a forwardly projecting extension having a closed sidewall defining a passageway extending from the rear end of the extension to the open front end thereof and in communication with the space in the speculum body. The extension tapers from its rear end to its narrow diameter front end which is adapted to be inserted into an ear canal to a point adjacent an eardrum. The device also includes a flexible, resilient, elastic, shape-retaining insufflator having a closed body defining a cavity in communication with the speculum body opening in the sidewall thereof. The insufflator is sealed to the exterior of the sidewall of the speculum body. The insufflator preferably is a torus surrounding the top and sidewall of the speculum body and in one embodiment the bottom of the speculuam body. Compression of the insufflator causes air to shoot out the front of the extension to imp act an eardrum to test its mobility. The extension and/or the lens may be removeable.

8 Claims, 3 Drawing Sheets

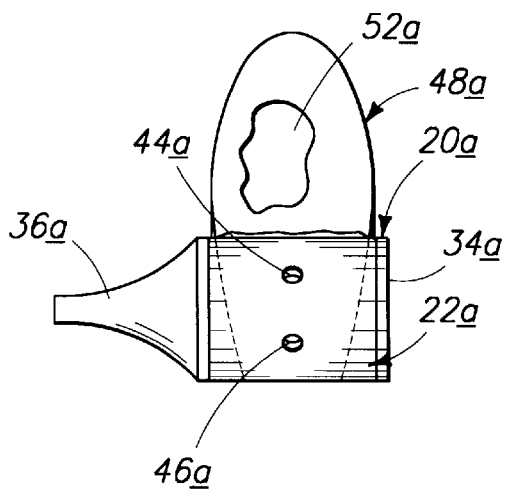
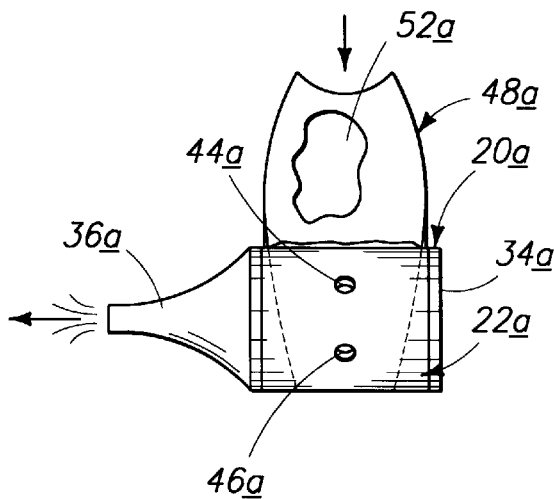
Fig 7
Fig 8
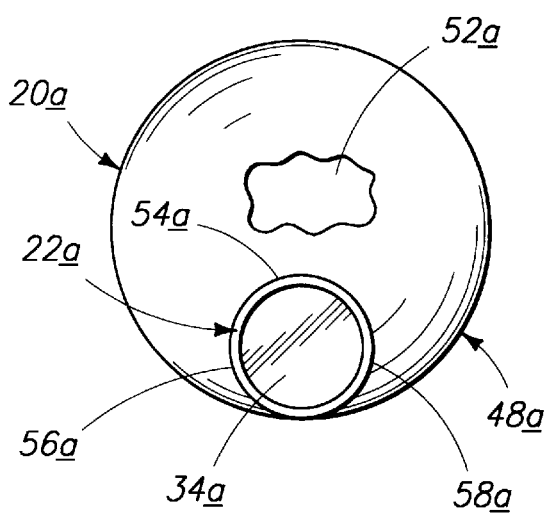
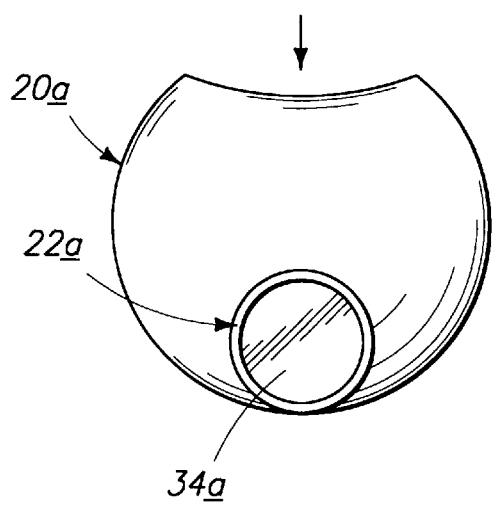
Fig 9
Fig 10

PNEUMATIC OTOSCOPE

BACKGROUND OF THE INVENTION

1. Field of the Invention

The present invention generally relates to a medical device and more particularly to an improved pneumatic otoscope for examination of an eardrum and ear canal.

2. Prior Art

Otoscopy is a medical procedure to visualize the ear canal and the tympanic membrane, that is, the eardrum. Currently available otoscopes each include a cone shaped speculum with the small end adapted to be inserted into the ear canal. A magnification lens is used to magnify the visual field. P Most otoscopes have a light source connected to them to illuminate the field of view. The speculum is detachable from the otoscope body which usually includes a straight handle of considerable bulk and length.

In order to see the entire ear canal and the tympanic membrane the canal must be straightened by pushing the tragus anteriorly with the side of the speculum while pulling the pinna backwards. This procedure therefore requires the use of both of the examiner's hands, one hand holding the otoscope while the other hand manipulates the pinna. If insufflation of the eardrum (tympanic membrane) is to be carried out, an insufflation bulb connected to the speculum by a flexible tubing is also held in the hand of the examiner manipulating the pinna.

Stabilization of the patient's head is also required in order to prevent head movement from obscuring the desired view of the ear canal and eardrum and also to prevent the speculum from striking and possibly damaging the eardrum. Stabilization is carried out by pressing the back of the hand holding the otoscope handle against the side of the patient's head at the parietal area of the head. The fingers of that hand are all wrapped around the otoscope handle and are therefore unavailable for aiding in the head stabilization procedure.

Unfortunately, this arrangement is not optimal for head stabilization, since the back of the hand does not provide a large or sensitive surface area with which to carry out the stabilization. Moreover, the bulb and tubing when not in use interfere with the examiner and may annoy the patient. In addition, they increase the bulkiness of the otoscope, as does the long handle of the otoscope, rendering the device less portable than desired. Reducing the size of the otoscope increases its portability but decreases the size of the viewing lens, reducing its optical clarity. Moreover, decreasing the size of the otoscope does not reduce the problem of having an instrument in which its various parts project from different angles and do not form a compact unit.

Accordingly, there is a need for a compact, efficient otoscope which permits insufflation to be carried out by the hand which holds the otoscope but in a manner which frees fingers and the palm of that hand to fully and efficiently stabilize the head of the patient. The otoscope should be capable of being made in any suitable size for use with adults, children and infants and should be easily carried by the examiner and easily cleaned before reuse.

SUMMARY OF THE PRESENT INVENTION

The improved pneumatic otoscope of the present invention satisfies all the foregoing needs. Thus, the otoscope is compact and easily carried, since it has no dangling insufflation tubes and bulbs. Moreover, the otoscope is shaped so that it is held between the thumb and forefinger of one hand of the examiner such that the remaining fingers of that hand and the palm of that hand can be efficiently used, rather than the back of the hand, to stabilize the head of the patient.

The otoscope of the present invention includes a speculum in the form of an elongated hollow tubular body to the rear end of which is attached a magnifying lens and to the front end of which is attached a forwardly projecting extension which is adapted to be inserted into the ear canal and positioned adjacent the tympanic membrane. The speculum has a central space extending longitudinally from the rear end thereof closed by the lens to the open front end thereof in communication with the extension.

The extension is generally cone-shaped, tapering forwardly to a smaller diameter than the rear end. The extension is hollow with an air passageway extending from the open rear end in communication with the speculum central space to an open front end. The sidewall of the speculum has at least one opening extending therethrough into communication with the speculum central space.

The device also includes a flexible, resilient, elastic, shape-retaining insufflator having a closed body defining an air-filled cavity which is in communication with the speculum body opening. Preferably, the insufflator is a torus surrounding the top and sidewall of the speculum and in one embodiment the bottom of the speculum. The insufflator is sealed to the exterior of the speculum body to form a unitary structure therewith.

Compression of the insufflator by the thumb and finger of the examiner passes air from its cavity through the speculum sidewall opening into the speculum central space, through the passageway in the extension and out the front end thereof as a puff or blast which impacts an eardrum adjacent the front end of the extension, causing the eardrum to move, thus testing the mobility of the ear drum.

The extension and/or lens can be threaded on to the front and rear end of the speculum body, if desired, so as to be removeable for replacement and cleaning thereof. The extension can also be made so as to telescope into the speculum body in order to reduce the overall size of the otoscope for convenient carrying. Moreover, the otoscope can also include light means, such as a battery, light bulb and one or more optic fibers for directing light into the ear canal.

Various other features of the improved pneumatic otoscope of the present invention are set forth in the following detailed description and accompanying drawings.

DRAWINGS OF THE EMBODIMENTS OF THE OTOSCOPE OF THE INVENTION

FIG. 7 is a schematic side elevation, partly broken away, of a second preferred embodiment of the improved pneumatic otoscope of the present invention, shown in the uncompressed state;

FIG. 8 is a schematic side elevation, partly broken away, of the otoscope of FIG. 7, shown in the compressed state;

FIG. 9 is a schematic rear elevation, partly borken away, of the otoscope of FIG. 7, shown in the uncompressed state;

FIG. 10 is a schematic rear elevation of the otoscope of FIG. 7, shown in the compressed state;

DETAILED DESCRIPTION OF THE EMBODIMENTS OF THE INVENTION

Figure 1:
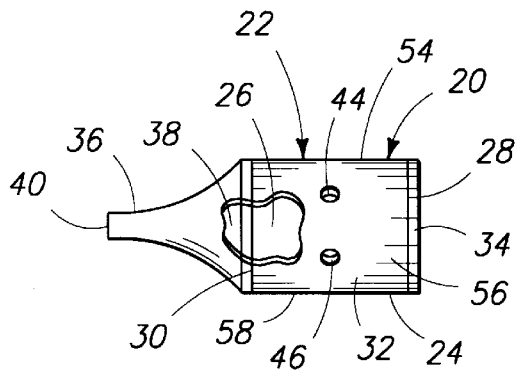
FIG. 1 is a schematic side elevation, partly broken away, of the speculum and extension portions of a first preferred embodiment of the improved pneumatic otoscope of the present invention.
Figure 2:
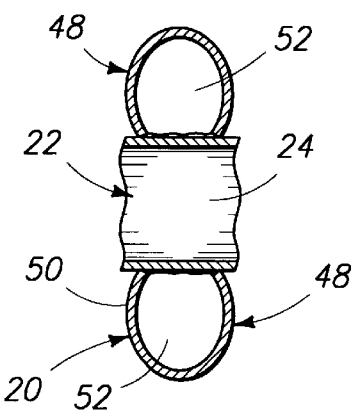
FIG. 2 is a schematic vertical cross-section, partly broken away, of the insufflator, speculum and extension of the first preferred embodiment of the otoscope of FIG. 1.
Figure 3:
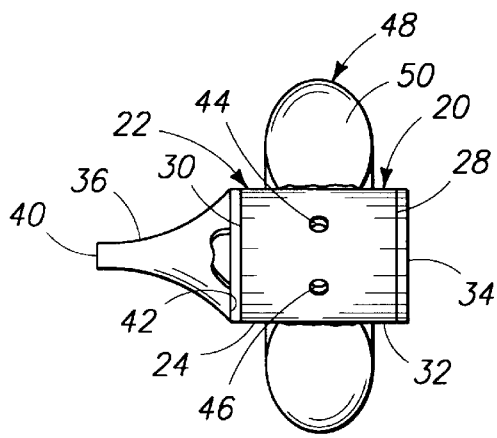
FIG. 3 is a schematic top plan view, partly broken away of the otoscope of FIG. 1.

FIGS. 1–6:

Now referring more particularly to FIGS. 1–6 of the drawings, a first preferred embodiment of the improved pneumatic otoscope of the present invention is schematically depicted therein. Thus, otoscope 20 is shown which includes a speculum 22 comprising an elongated hollow tubular body 24 having a generally central space 26 extending from the rear end 28 of body 24 to the front end 30 thereof and defined by a sidewall 32. Speculum 22 includes an optical lens 34 releasably threaded on to rear end 28 of body 24, so that lens 34 can be removed, cleaned and replaced, as desired. Lens 34 seals rear end 28 of body 24.

Speculum 22 also has a cone-shaped hollow extension 36 connected body 24 and projecting forwardly thereof for insertion into an ear canal. Extension 36 tapers forwardly and has a central passageway 38 extending the length thereof from open front tip 40 to open rear end 42 of extension 36. Rear end 42 is threaded to front end 30 of speculum body 24 so that extension 36 forms a unitary body with speculum 22, but is removeable therefrom for cleaning and replacement. Passageway 38 communicates with central space 26.

Sidewall 32 of speculum body 24 has a pair of openings 44 and 46 extending therethrough into communication with central space 26. An insufflator 48 is sealed to the exterior surface of sidewall 32 so that insufflator 48 forms a unitary body with speculum 22. Insufflator 48 is a flexible, resilient, shape-retaining body 50 defining a central cavity communicating with openings 44 and 46 through one or more openings (not shown).

Figure 4:
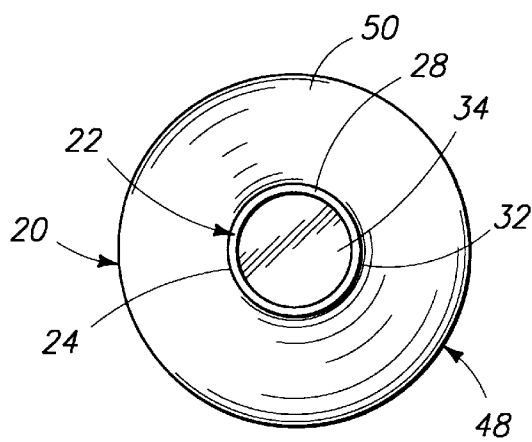
FIG. 4 is a schematic rear elevation of the otoscope of FIG. 1, shown in the uncompressed state.
Figure 5:
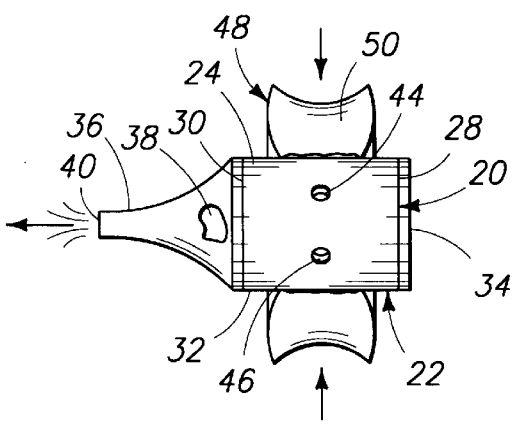
FIG. 5 is a schematic side elevation, partly broken away, of the otoscope of FIG. 1, shown in the compressed state.
Figure 6:
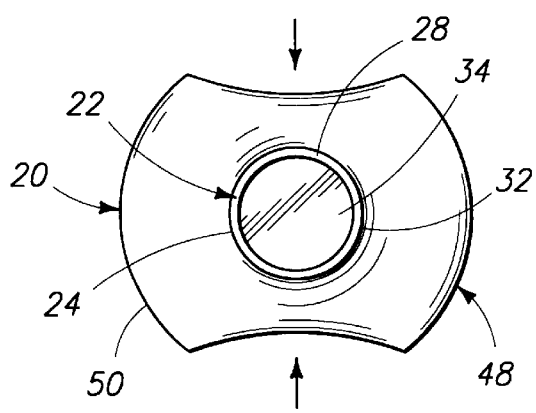
FIG. 6 is a schematic rear elevation of the otoscope of FIG. 1, shown in the compressed state.
Figure 11:
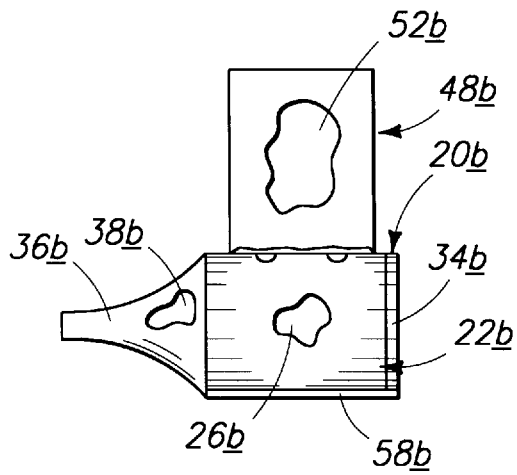
FIG. 11 is a schematic side elevation, partly broken away, of a third preferred embodiment of the improved pneumatic otoscope of the present invention, shown in the uncompressed state.
Figure 12:
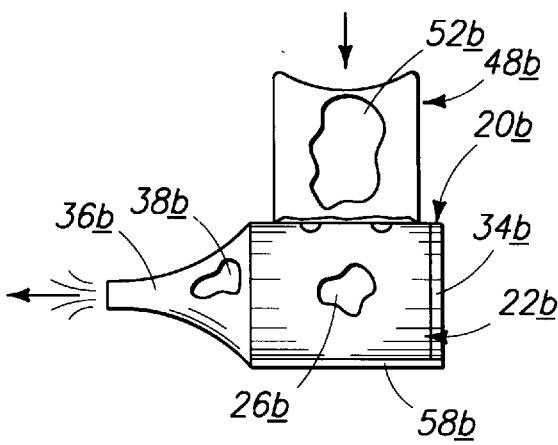
FIG. 12 is a schematic side elevation, partly broken away, of the otoscope of FIG. 11, shown in the compressed state.
Figure 13:
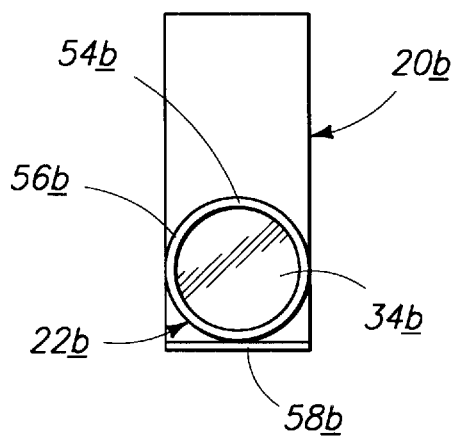
FIG. 13 is a schematic rear elevation of the otoscope of FIG. 11, shown in the uncompressed state; and, FIG. 14 is a schematic rear elevation of the otoscope of FIG. 11, shown in the compressed state.
Figure 14:
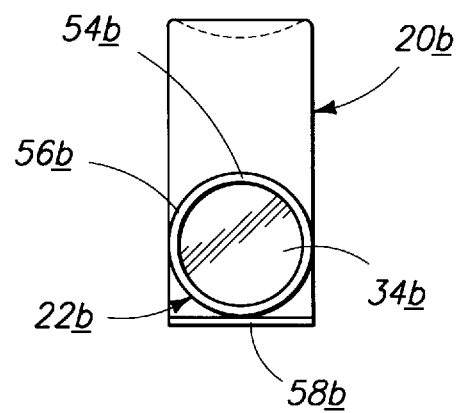

Insufflator 48 is in the shape of a torus or doughnut, much like the inner tube of a tire, and is preferably at least semi-circular in outline, covering the top 54 and sides 56 of speculum 22. As shown in FIG. 4, in this embodiment insufflator 48 entirely surrounds the top 54, sides 56 and bottom 58 of speculum 22. Insufflator cavity 52 is filled with air. Insufflator 48 is compressible from its doughnut shape (FIG. 4) to a somewhat flattened shape (FIG. 6) but when compression is terminated, it returns by elastic memory to its uncompressed doughnut shape.

When a care-giver wishes to examine a patient's ear canal and eardrum, particularly to test the latter for mobility, the care-giver grasps the insufflator portion 48 of the otoscope 20 between the thumb and a finger, preferably the forefinger, with the speculum 22 and extension 36 pointed toward the patient. The palm and remaining fingers of the hand of the care-giver which holds the otoscope 20 are placed against the head of the patient to steady it, while the other hand of the care-giver pulls the patient's pinna in a direction which gives proper viewing of the ear canal.

Thereupon, the care-giver inserts the extension 36 into the ear canal so that its front tip 40 is positioned next to but not touching the eardrum. The insufflator 48 is then sqweezed between the thumb and finger to force a puff of air against the eardrum while the care-giver views the eardrum through the optical lens 34 of the speculum 22. The degree of movement of the eardrum aids the care-giver in determining the elasticity of the eardrum as a measure of its health.

When the care-giver releases the compressing force on the insufflator 48, the insufflator 48 returns to its original unflexed shape, after which the care-giver can repeat the procedure or terminate it. Accordingly, otoscope 20 permits rapid and accurate examination of the ear canal and eardrum, while optimal steadying of the head of the patient against movement is easily carried out.

Moreover, otoscope 20 is of compact size, can be made of readily available materials and is inexpensive, easy to use and durable. Speculum 22 and extension 36 can be of metal, plastic, ceramic or the like, while lens 34 can be of glass or plastic. Insufflator 48 can be of elastic plastic or rubber. Otoscope 20 represents a substantial advance over the prior art, insufflator 48 acting as a protective cushion for speculum 22 and extension 36.

FIGS. 7–10:

A second preferred embodiment of the improved otoscope of the present invention is schematically depicted in FIGS. 7–10. Thus, otoscope 20a is shown. Components thereof similar to those of otoscope 20 bear the same numerals but are succeeded by the letter "a".

Otoscope 20a differs from otoscope 20 only in that insufflator 48a is not concentric with speculum 22a, extending mainly above and to the sides of speculum 22a, as shown in FIGS. 7–10. However, otoscope 20a functions similarly to otoscope 20 and has its other advantages.

FIGS. 11–14:

A third preferred embodiment of the improved otoscope of the present invention is schematically depicted in FIGS. 11–14. Thus, otoscope 20b is shown. Components similar to those of otoscope 20 bear the same numerals but are succeeded by the letter "b".

Otoscope 20b differs from otoscope 20 only as follows:

a) Insufflator 48b is a compressible block connected to top 54b and upper sides 56b of speculum 22b and extends thereabove, the bottom 58b of speculum 22b being substantially horizontal to facilitate holding of otoscope 20b on the thumb of the care-giver;

b) Openings 44b and 46b are on top 54b; and, c) Lens 34b is permanently connected to speculum body 24b.

Otoscope 20b functions similarly to 20 while being slightly more compact for easier carrying.

Various other modifications, changes, alterations and additions can be made in the improved pneumatic otoscope of the present invention, its components and their parameters. All such modifications, changes, alterations and additions as are within the scope of the appended claims form part of the present invention.

What is claimed is:

1. An improved pneumatic otoscope for examination of an eardrum, said otoscope comprising, in combination:

a. a speculum comprising, in combination, an elongated generally tubular body having an open front end, a closed rear end and integral closed sidewall defining a generally central space extending from said rear end to said front end, said speculum including a viewing lens connected to and closing said rear end and an elongated extension connected to said front end, said extension tapering forwardly to a diameter less than that of said speculum body and adapted to be inserted into an ear adjacent an eardrum, said extension having an open front end, an open rear end and a central passageway communicating with said open front end of said speculum body and with said central space, said speculum body defining at least one peripheral opening extending through said sidewall to said central space; and, b. a flexible, resilient, elastic, shape-retaining insufflator sealed to said speculum body and extending outwardly therefrom generally perpendicular to the longitudinal axis of said speculum body, said insufflator comprising a closed body defining a generally central cavity communicating with said peripheral opening in said speculum body, whereby compression of said insufflator forces air from said cavity through said speculuim opening and out said front end of said extension for impact against an eardrum to test the mobility of that eardrum.

2. The improved otoscope of claim 1 wherein said insufflator extends above said speculum.

3. The improved otoscope of claim 1 wherein said insufflator is a torus and extends around at least the top and sides of said speculum body.

4. The improved otoscope of claim 3 wherein said torus extends completely around the top, sides and bottom of said speculum body.

5. The improved otoscope of claim 1 wherein said speculum body is generally cylindrical.

6. The improved otoscope of claim 1 wherein said speculum body has a flat horizontal finger-supporting base.

7. The improved otoscope of claim 1 wherein at least one of said extension and said lens is detachable from said speculum body for cleaning and replacement thereof.

8. The improved otoscope of claim 1 wherein said speculum body and extension comprise at least one of plastic and metal and wherein said insufflator comprises one of plastic and rubber.

* * * * *